United States Patent

Wu

Patent Number: 5,099,829
Date of Patent: Mar. 31, 1992

[54] MASSAGE DEVICE GOOD FOR EYES

[76] Inventor: An-Chuan Wu, P.O. Box 26-301, Taipei, Taiwan

[21] Appl. No.: 514,234

[22] Filed: Apr. 25, 1990

[51] Int. Cl.$^5$ ............................................. A61H 1/00
[52] U.S. Cl. .................................... 128/32; 128/35; 128/36; 128/25 A; 128/41; 128/62 R
[58] Field of Search ................ 128/32, 35, 36, 41, 128/45, 46, 51, 52, 62 R, 25 A, 76.5, 380, 793

[56] References Cited

U.S. PATENT DOCUMENTS

| | | | |
|---|---|---|---|
| 2,882,892 | 4/1959 | Kosior | 128/62 R |
| 3,971,387 | 7/1976 | Mantell | 128/792 |
| 4,331,163 | 5/1982 | Nomura | 128/793 |
| 4,574,787 | 3/1986 | Jacobs | 128/64 |
| 4,787,372 | 11/1988 | Ramseyer | 128/62 X |
| 4,841,954 | 6/1989 | Kalsi | 128/36 |

*Primary Examiner*—Robert A. Hafer
*Assistant Examiner*—Brian E. Hanlon
*Attorney, Agent, or Firm*—Wayne L. Lovercheck; Charles L. Lovercheck

[57] ABSTRACT

Disclosed is a massage device good for eyes, specifically a massage mask which has the effects of low frequency therapy and of stimulating the acupuncture points relating to the eyes. The mask is provided with a plurality of conductive projections conformable with the relative facial configurations at the related positions about the eyes and a low frequency wave generator which is provided with means for adjusting its current intensity and/or frequency and means for timing interruption.

2 Claims, 3 Drawing Sheets

MASSAGE DEVICE GOOD FOR EYES

BACKGROUND OF THE INVENTION

Till now, no effective medicine or therapy has been found in the domain of western medicine to solve the problem of near sight or loss of sight. However, it has been found that massaging the acupuncture points relating to the eyes in accordance with the Chinese technique of acupuncture is relatively effective in solving the problem.

Moreover, physical therapy using low frequency electrical current is widely adopted in the domain of medicine and there are, therefore, various low frequency massage devices available. Nevertheless, the effectiveness of these devices is not remarkable because most of the users are not aware of the accurate positions of the concerned acupuncture points on the human body and the related effects which can be achieved by massaging these points.

Accordingly, the primary object of the invention is to provide a massage device good for eyes, in which a plurality of conductive projections are fixedly provided so that low frequency currents passed through these projections can be utilized for massaging and stimulating the acupuncture points relating to the eyes in order to eliminate the fatigue thereof and maintain their health.

Another object of the invention is to provide a health maintaining device for the eyes which is capable of accurately stimulating the concerned acupuncture points without the use of fingers so that the drawbacks of massaging the acupuncture points by fingers, such as contamination of the eyes by the unclean fingers and the use of incorrect massage positions, can be eliminated.

BRIEF SUMMARY OF THE INVENTION

To achieve these objects, a massage device good for eyes in accordance with this invention comprises an eyes mask provided with a plurality of projections of different shapes conformable with the facial configurations at the corresponding acupuncture points to be massaged. These projections are energized by a low frequency generator the current intensity and/or frequency of which can be adjusted to properly massage the muscles about the eyes and stimulate the acupuncture points relating to the eyes. The device may also be provided with means for timing interruption so that the duration of its operation can be controlled by the user.

BRIEF DESCRIPTION OF THE DRAWINGS

A preferred embodiment of the invention will now be described by way of example and with reference to the accompanying drawings, in which.

DETAILED DESCRIPTION OF THE INVENTION

Figure 1:
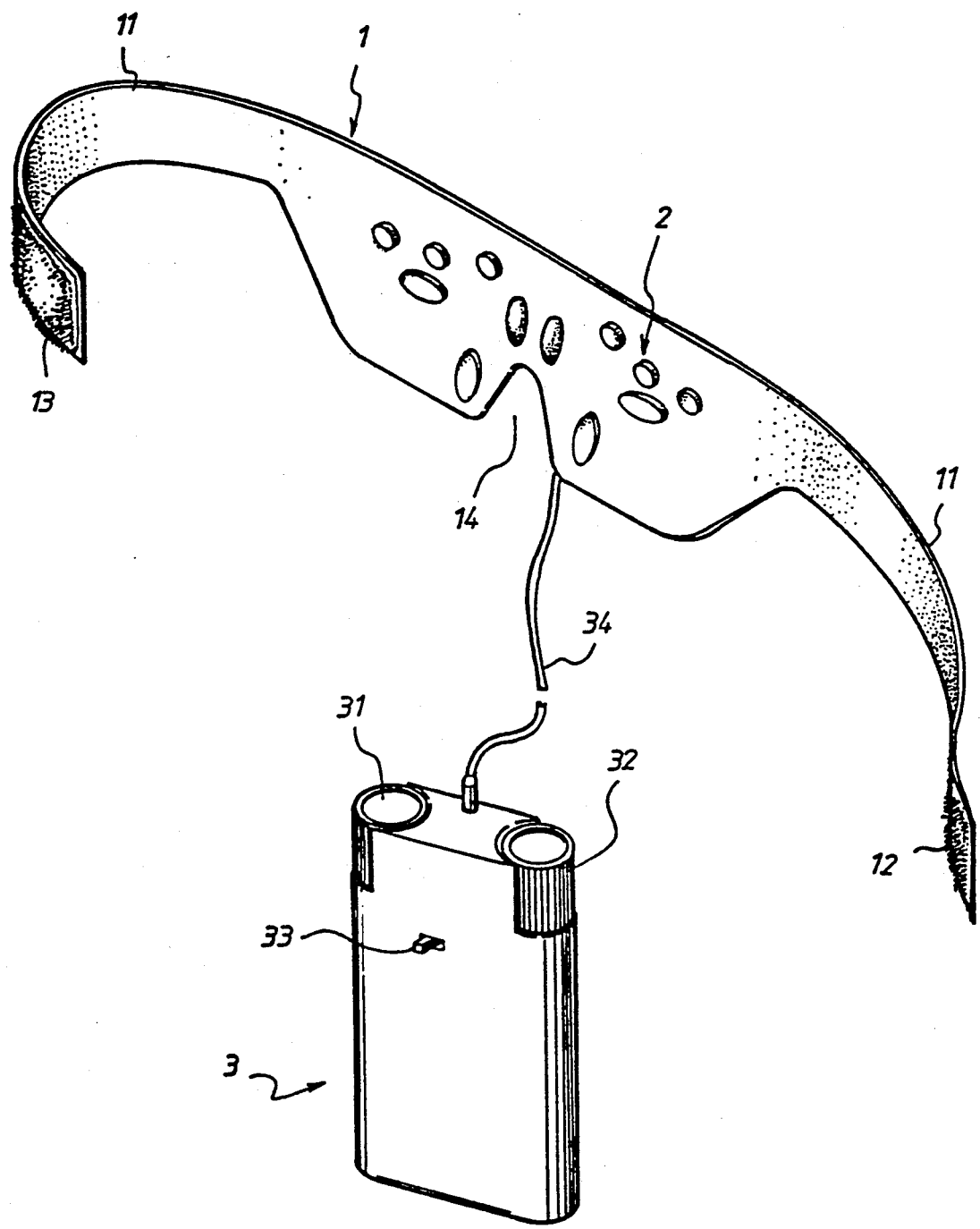
FIG. 1 is an outside view of the massage device in accordance with the invention.

Referring to FIG. 1, the massage device in accordance with the invention primarily comprises an eyes mask 1, on the inner side of which are symmetrically provided two sets of conductive projections 2. On each side of the mask is an extended band 11. At the free ends of the bands 11 are provided hook and loop bands 12 and 13 respectively. Hook and loop fasteners sold under the trademark "Velcro" are representative of the fasteners which may be used. The mask is formed at the central portion thereof with a notch 14 to accommodate the nose of the user. The device also comprises a low frequency generator 3 including a current intensity adjusting knob 31, a frequency adjusting knob 32, and a timing interruption switch 33. The projections are connected with the generator 3 by a conductive wire 34.

Figure 2:
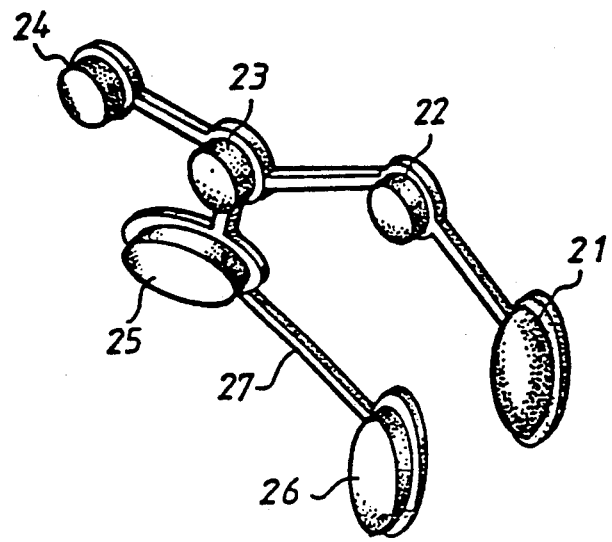
FIG. 2 is a pictorial view showing the arrangement of the massage projections in accordance with the invention.
Figure 3A:
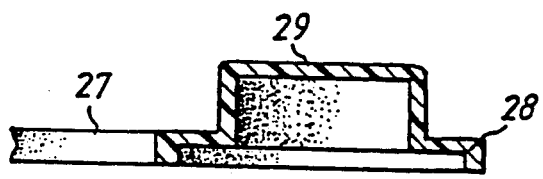
FIG. 3A and 3B are the sectional views illustrating the construction of one of the projections.
Figure 3B:
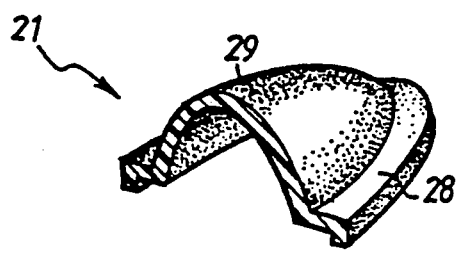

As shown in FIG. 2, a set of projections consists of six massage projections connected together by conductive strips 27. These projections are different in position, shape, and/or function. The basic construction of each of the projections is as shown in FIG. 3A. Each projection may be integrally formed from metal impregnated conductive rubber to form a hollow projection portion 29 and a base portion 28. In each set 2 of projections, there are an ellipsoidal projection 21 (the construction of which is shown in FIG. 3B), three flat circular projections 22, 23, 24, and two flat elliptical projections 25, 26.

Figure 4:
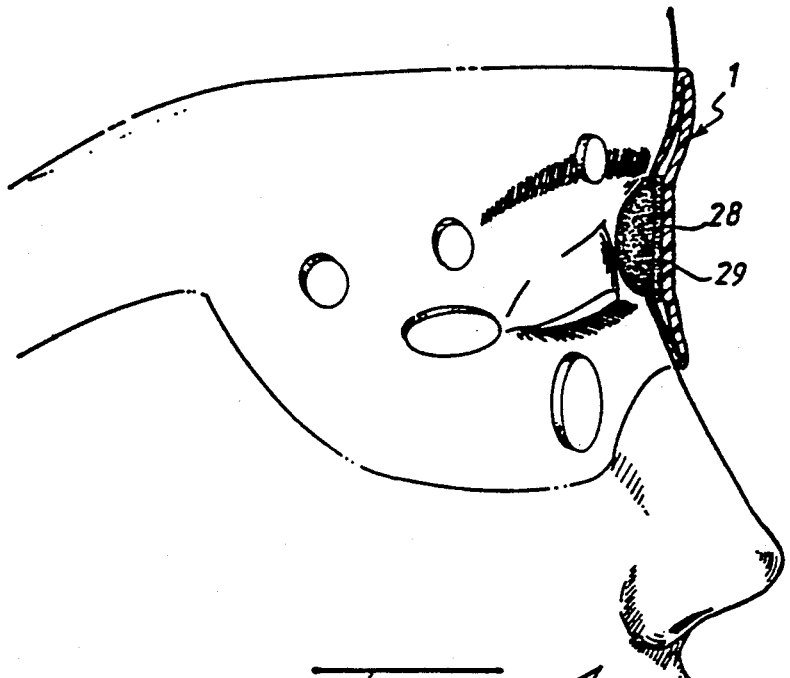
FIG. 4 illustrates the use of the massage device in accordance with the invention.

As can be seen in FIG. 4, the base portion 28 of each projection is enclosed in the mask but the projection portion 29 is exposed.

The mask consists of a double layer of flexible material. The inner layer has through holes at each of the projection positions so that the base portions 28 of the projections and the connecting conductive strips 27 are enclosed and the projection portions 29 of the projections are exposed so that they can contact the appropriate positions on the user's face.

Also referring to FIG. 1, to use the mask, the user may first wet (e.g. by wetted cotton) the face portion about the eyes to increase conductivity and then wear the mask 1. The mask should be properly positioned so that the two flat ellipsoidal projections rest against the skin on the two sides of the bridge of nose as shown in FIG. 4. The two bands 11 are fastened together by hook and loop bands 12 and 13. Hook and loop fasteners sold under the trademark "Velcro" are representative of the fasteners which may be used. Now the projections are positioned at the corresponding acupuncture points and the user may switch on the generator 3. The user may adjust the frequency provided by the generator 3 through knob 32 according to his own sense of comfort.

Figure 5:
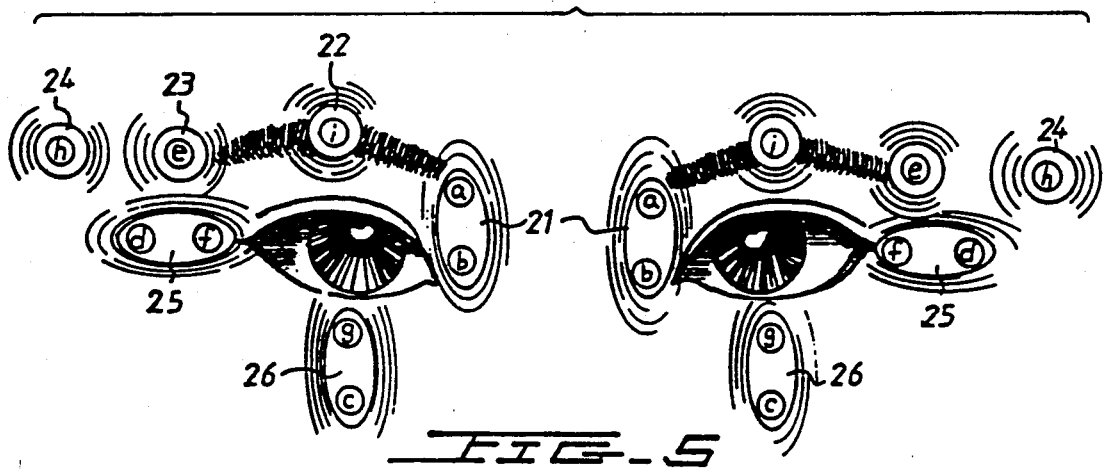
FIG. 5 illustrates the relative positions of the acupuncture points corresponding to the projections of the device in accordance with the invention.

Referring to FIG. 5, the projections are arranged in accordance with the principles of acupuncture. When the user wears the mask 1, each ellipsoidal projection 21 is positioned on the acupuncture points of Tzanchu (at the medial end of the eyebrow) (a) (which, when stimulated, has curing effect on tears shedding, sclerokeratitis, eye obscure, and white spots on cornea) and Chingming (on the margin of the orbit and 0.1 inch above the corner of the inner canthus, alongside the medial border of the eyeball) (b) (which, when stimulated, has curing effect on acute and chronic conjunctivitis, myopia, tears shedding against the wind, hyperopia, photophobia, optic neutiris, optic atrophy, and cataract). The first flat circular projection 22 is positioned on the acupuncture point of Yangbai (one inch above the middle of the eyebrow, in the depression on the superciliary arch) (i) (which, when stimulated, has curing effect on headache, eye disease, facial neuroparalysis). The second flat circular projection 23 is positioned on the acupuncture point of Sichukong (at the lateral end of the eyebrow) (e) (which, when stimulated, has curing effect on migraine, eye disease, facial carbuncle). The third flat circular projection 24 is positioned on the acupuncture point of Hanyen (one inch below the lateral part of Touwei—within the natural line of the hair in front of the temple) (h) (which, when stimulated, has curing effect on giddy and facial carbuncle). The first flat ellipticle projection 25 is positioned on the acupuncture points of Tiyang (in the depression about one inch lateral to the external canthus) (d) (which, when stimulated, has curing effect on headache and eye disease) and Tungtsuchiao (about 0.1 inch lateral to the external canthus) (f) (which, when stimulated, has curing effect on eye obscure, white spots on cornea, conjunctivitis, and optic atrophy). The second flat elliptical projection 26 is positioned on the acupuncture points of Chengchi (between the eyeball and the inferior border of the orbit, with the eyes looking straight ahead) (g) (which, when stimulated, has curing effect on acute and chronic conjunctivitis, eye muscle paralysis, tears shedding, myopia, hyperopia, nyctalopia, and optic atrophy) and Sibai (in the depression at the infraorbital foramen) (c) (which, when stimulated, has curing effect on facial carbuncle, trifacial neuralgia, and eye disease).

While only one preferred embodiment of the invention has been shown and described, it will be understood that this invention is not limited thereto since modifications can be made and will become apparent to those skilled in the art.

I claim:

1. A massage device which utilizes low frequency electrical current in conductive material to stimulate the eyes comprising:

an eyes mask consisting of a doublelayer construction with a plurality of through holes, at the end of each of the bands extending from the sides of the mark is provided a hook and loop band for fastening the mask on the user's head;

two symmetric sets of conductive projections are provided connected together by conductive strips, each set comprising an ellipsoidal projection, two flat elliptical projections, three flat circular projections distributed around the mask portion to be covered on the corresponding eye, each conductive projection may be integrally formed from metal impregnated conductive rubber to constitute a base portion and a projection portion; and disposing each set of the projections in a half of the mask so that the base portion of each of the projections is enclosed in the doublelayer construction and the projection portion of each of the projections is exposed from the construction and connecting the sets of projections with a low frequency generator by a conductive wire so that low frequency current through the projections can be utilized to massage and stimulate the corresponding acupuncture points;

the distribution of the projections on the mask is arranged so that in each of the two sets an ellipsoidal projection will engage the user along a line extending from a point at the medial end of the eyebrow, to a point on the margin of the orbit and 0.1 inch above the corner of the inner canthus, alongside the medial border of the eyeball;

a first flat circular projection will engage the user one inch above the middle of the eyebrow, in the depression on the superciliary arch;

a second flat circular projection will engage the user at the lateral end of the eyebrow;

a third flat circular projection will engage the user approximately one inch lateral from the end of the eyebrow in front of the temple;

a first flat ellipticle projection will engage the user along a line extending from a point in the depression about one inch lateral to the external canthus to a point about 0.1 inch lateral to the external canthus, and a second flat elliptical projection will engage the user along a line extending from a point between the eyeball and the inferior border of the orbit with the eyes looking straight ahead to a point in the depression at the infraorbital foramen.

2. An massage device according to claim 1, wherein the low frequency generator may be provided with a timing interruption switch so that the generator can be switched off at a predetermined time.

* * * * *